(12) United States Patent
Baker et al.

(10) Patent No.: US 9,295,303 B2
(45) Date of Patent: Mar. 29, 2016

(54) ARTICLE OF FOOTWEAR FOR PROPRIOCEPTIVE TRAINING

(71) Applicant: NIKE, Inc., Beaverton, OR (US)

(72) Inventors: Brian D. Baker, Portland, OR (US); Martine I. V. Mientjes, Beaverton, OR (US); Erez Morag, Lake Oswego, OR (US); Nicola J. Reynolds, Hillsboro, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/306,652

(22) Filed: Jun. 17, 2014

(65) Prior Publication Data

US 2014/0331524 A1 Nov. 13, 2014

Related U.S. Application Data

(62) Division of application No. 12/986,583, filed on Jan. 7, 2011, now Pat. No. 8,840,530.

(51) Int. Cl.
*A63B 23/08* (2006.01)
*A43B 7/14* (2006.01)
*A63B 21/00* (2006.01)
*A63B 21/055* (2006.01)
*A63B 23/035* (2006.01)
*A43B 5/00* (2006.01)

(52) U.S. Cl.
CPC ... *A43B 7/14* (2013.01); *A43B 5/00* (2013.01); *A63B 21/0004* (2013.01); *A63B 21/0552* (2013.01); *A63B 21/4011* (2015.10); *A63B 21/4015* (2015.10); *A63B 23/03508* (2013.01)

(58) Field of Classification Search
CPC ........... A63B 21/0004; A63B 21/0552; A63B 21/4011; A63B 21/4015; A63B 23/03508; A63B 5/00; A43B 7/14
See application file for complete search history.

(56) References Cited

U.S. PATENT DOCUMENTS

| | | |
|---|---|---|
| 604,044 A | 5/1898 | Hamel et al. |
| 979,243 A | 12/1910 | Anderson |
| 1,553,874 A | 9/1925 | Nivens |
| 4,280,488 A | 7/1981 | Polsky et al. |
| 4,294,238 A | 10/1981 | Woodford |
| 4,367,885 A | 1/1983 | Ramer |
| 4,878,504 A | 11/1989 | Nelson |
| 5,090,138 A | 2/1992 | Borden |
| 5,125,171 A | 6/1992 | Stewart |
| 5,215,508 A | 6/1993 | Bastow |
| 5,219,324 A | 6/1993 | Hall |
| 5,224,925 A | 7/1993 | Varn |
| 5,256,119 A | 10/1993 | Tudor |
| 5,399,155 A | 3/1995 | Strassburg et al. |
| 5,475,935 A | 12/1995 | Frost |
| 5,621,985 A | 4/1997 | Frost |
| 5,833,640 A | 11/1998 | Vazquez, Jr. et al. |
| 5,843,010 A | 12/1998 | Bodmer |
| 7,261,679 B2 | 8/2007 | Sload |
| 7,510,538 B2 | 3/2009 | Wolter et al. |
| 7,644,521 B2 | 1/2010 | McCarron |
| 7,678,067 B1 | 3/2010 | Smith et al. |
| 7,753,664 B2 | 7/2010 | Beckwith et al. |
| 8,246,562 B2 | 8/2012 | Colon |
| 2013/0196829 A1 | 8/2013 | Elbaz et al. |

*Primary Examiner* — Glenn Richman
(74) *Attorney, Agent, or Firm* — Plumsea Law Group, LLC

(57) ABSTRACT

A method of proprioceptive training using an article of athletic equipment having an article of footwear, a knee coupling member, and a biasing member is disclosed. The method includes securing the article of footwear to a foot and securing the knee coupling member to a leg superiorly and inferiorly about a knee joint thereof. Moreover, the method includes biasing the article of footwear relative to the knee coupling member using the biasing member to bias the foot toward plantarflexion relative to the leg to increase proprioception of the foot relative to the leg.

20 Claims, 2 Drawing Sheets

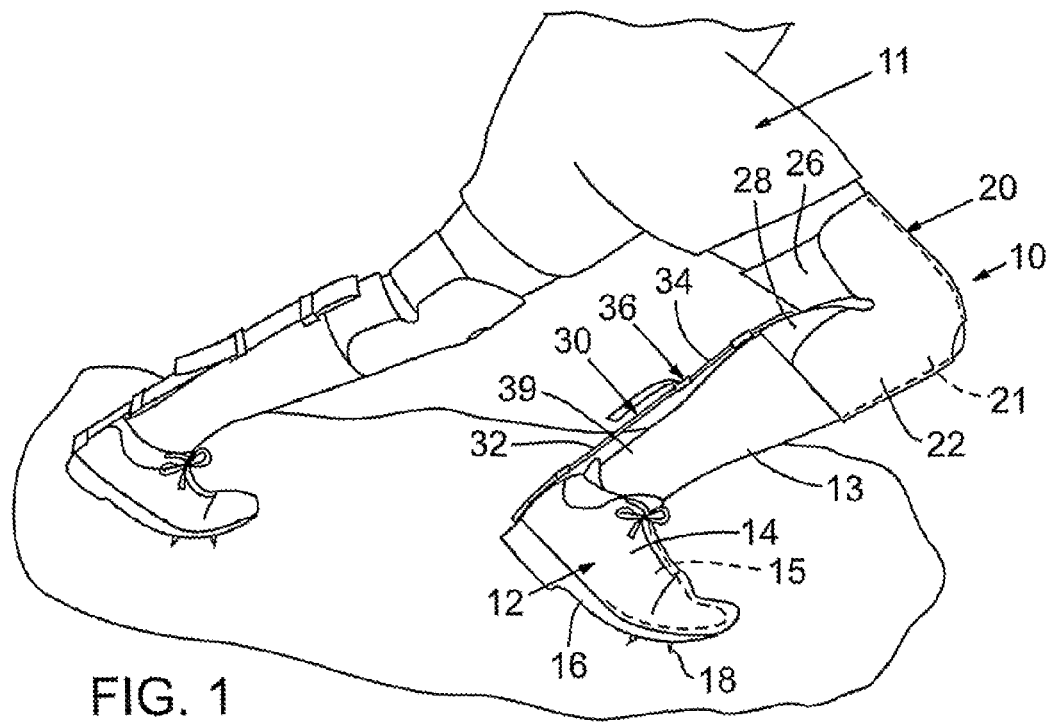
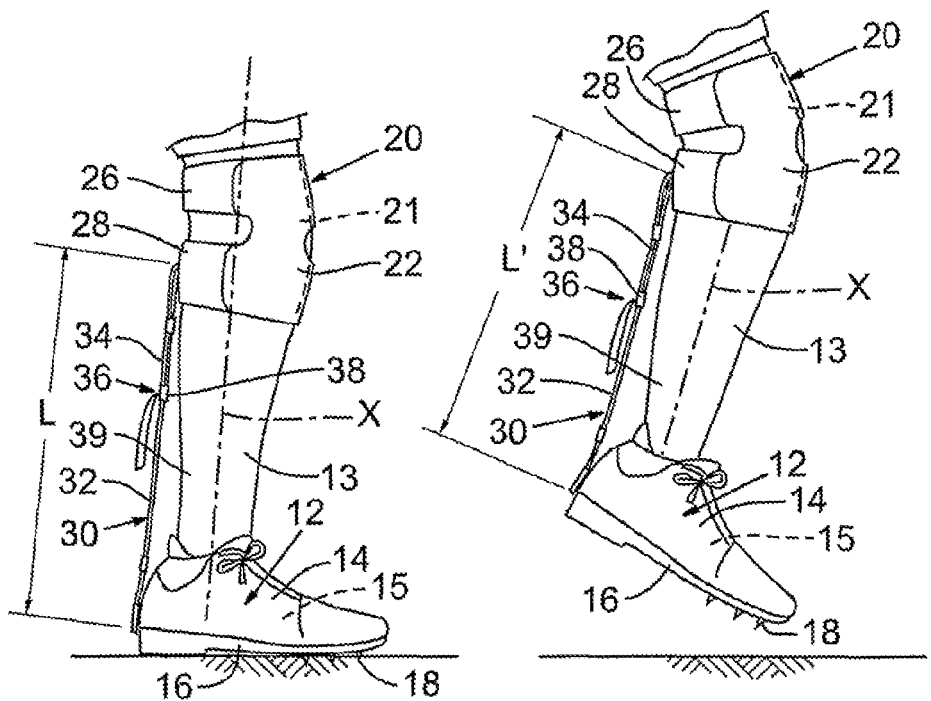

ARTICLE OF FOOTWEAR FOR PROPRIOCEPTIVE TRAINING

CROSS-REFERENCE TO RELATED APPLICATION

This application is a divisional of co-pending application Ser. No. 12/986,583, filed Jan. 7, 2011, the disclosure of which is hereby incorporated by reference in its entirety.

FIELD

The present disclosure relates to an article of footwear and, more particularly, relates to an article of footwear for proprioceptive training.

BACKGROUND

Proprioception is a conscious or unconscious awareness of a body part's position relative to another. Proprioception enables a person to move their body in a desired manner.

Learning a new skill, sport, or other activity can often include improving proprioception. For instance, as a person learns to play the guitar, the student improves proprioception of the relative position of the fingers. As an illustration, the guitar student learns to play typically while looking at his or her hands and slowly positioning the fingers to play the desired chords. However, as proprioception improves, fingering becomes easier and the student may eventually be able to play without looking at his or her hands.

Sports training can also include improvements to an athlete's proprioception. For instance, a soccer player can practice trapping, passing, juggling and other skills to improve proprioception of the feet and legs. Such training can improve the player's abilities, making the player's movements quicker, more fluid, and generally more effective.

Moreover, it has been shown that a runner's performance (acceleration, etc.) can be improved by increasing plantarflexion of the feet (increasing the angle of the foot away from the shin) during the running stride. In some cases, a runner can train themselves to increase plantarflexion by trying to consciously run with their weight shifted forward and/or attempt to consciously plantarflex more quickly while running. However, improving running performance in this manner can be slow and tedious and possibly ineffective. Accordingly, there is a need for athletic equipment that can improve proprioception and actively increase plantarflexion, for instance, to thereby increase running performance.

SUMMARY

An article of athletic equipment for a wearer with a foot and a leg including a knee joint is disclosed. The article of athletic equipment includes an article of footwear operable to secure to the foot. The equipment also includes a knee coupling member that is operable to secure to the leg about the knee joint. The knee coupling member is operable to extend superiorly and inferiorly about the knee joint. Moreover, the equipment includes a biasing member that is coupled to the article of footwear and the knee coupling member. The biasing member biases the article of footwear relative to the knee coupling member to bias the foot toward plantarflexion relative to the leg to increase proprioception of the foot relative to the leg.

A method of proprioceptive training using an article of athletic equipment having an article of footwear, a knee coupling member, and a biasing member is also disclosed. The method includes securing the article of footwear to a foot and securing the knee coupling member to a leg superiorly and inferiorly about a knee joint thereof. Moreover, the method includes biasing the article of footwear relative to the knee coupling member using the biasing member to bias the foot toward plantarflexion relative to the leg to increase proprioception of the foot relative to the leg.

Still further, an article of athletic equipment for a wearer with a foot and a leg including a knee joint is disclosed. The article of athletic equipment includes an article of footwear operable to secure to the foot. The article of footwear includes a heel portion, an upper, and a sole assembly that is operably coupled to the upper. The equipment further includes a knee coupling member that is operable to secure to the leg about the knee joint. The knee coupling member includes a superior strap that extends across a superior portion of the knee joint and an inferior strap that extends across an inferior portion of the knee joint. The superior and inferior straps are separated at a distance. Moreover, the equipment includes a resiliently flexible biasing member that is fixed to the article of footwear adjacent the heel portion. The biasing member is also fixed to the inferior strap of the knee coupling member. The biasing member extends along a posterior side of the leg along a longitudinal axis of the leg to bias the foot toward plantarflexion relative to the leg to increase proprioception of the foot relative to the leg. The biasing member includes a resiliently flexible first portion, a resiliently flexible second portion, and a buckle that adjustably couples the first and second portions together. The buckle is adjustable to vary a tension of the biasing member.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 1 is a perspective view of athletic equipment for proprioceptive training according to various exemplary embodiments of the present disclosure;

FIG. 2 is a side view of the athletic equipment of FIG. 1 shown in a standing position;

FIG. 3 is a side view of the athletic equipment of FIG. 1 shown in a plantarflexed position;

Corresponding reference numerals indicate corresponding parts throughout the several views of the drawings.

DETAILED DESCRIPTION

Figures 4, 5:
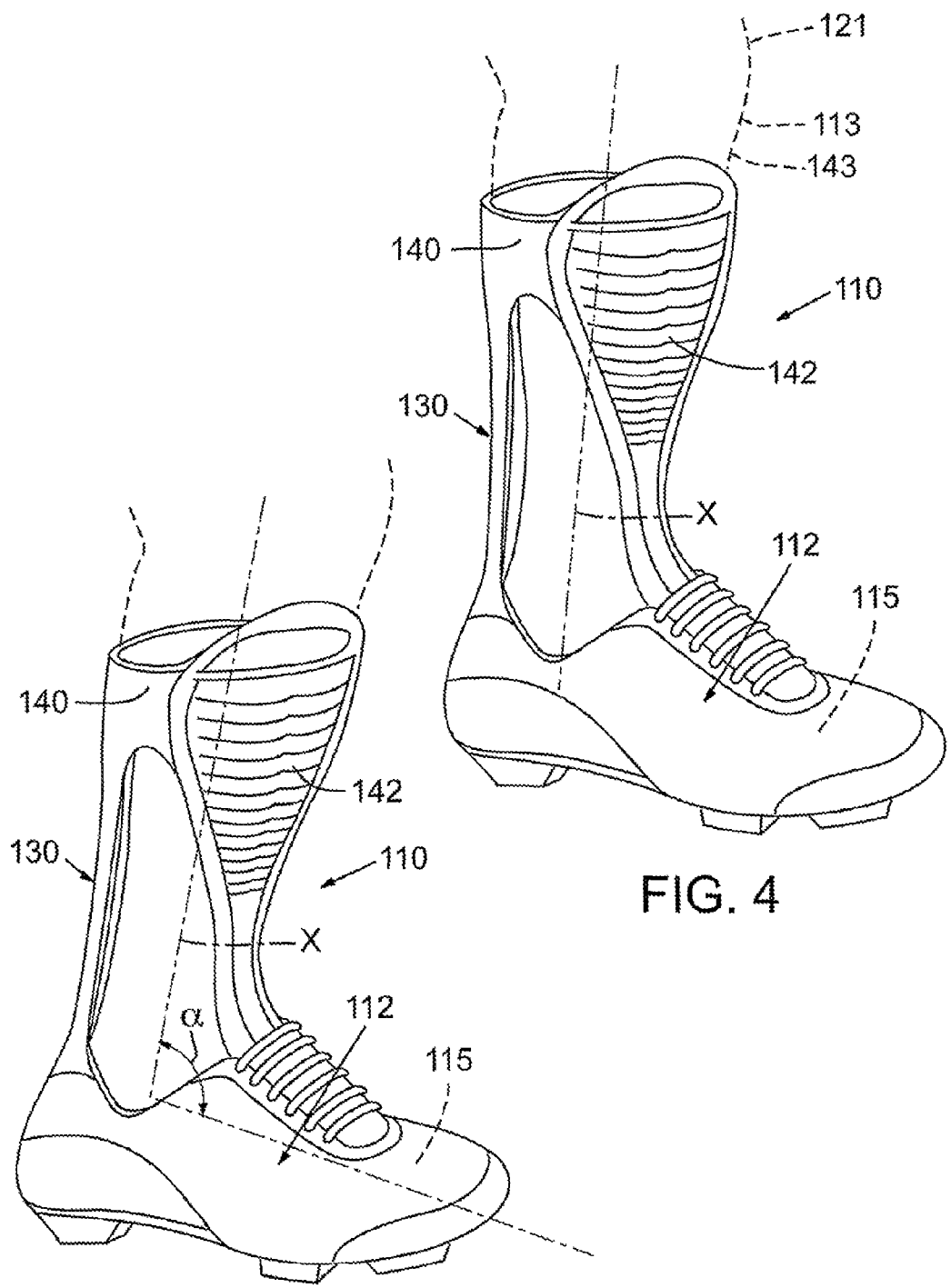
FIG. 4 is a perspective view of the athletic equipment according to various additional exemplary embodiments of the present disclosure.
FIG. 5 is a perspective view of the athletic equipment of FIG. 4 shown in a dorsiflexed position.

Example embodiments will now be described more fully with reference to the accompanying drawings.

Referring initially to FIGS. 1-3, an article of athletic equipment 10 is illustrated according to various exemplary embodiments of the present disclosure. As shown, a wearer 11 (user) can wear the equipment 10 on his or her respective leg 13 and foot 15. As will be discussed, the equipment 10 can increase plantarflexion of the foot 15 relative to the leg 13 to advantageously increase proprioception of the foot 15 relative to the leg 13 and to advantageously improve running performance (e.g., acceleration, top speed, etc.)

In the embodiment shown, separate articles of athletic equipment 10 are shown worn on both the right and left legs 13; however, it will be appreciated that the article of athletic equipment 10 can be worn alone on either of the right and left legs 13. The equipment 10 worn on the right leg 13 will be explained in detail; however, it will be appreciated that the equipment 10 worn on the left leg 13 can be substantially similar.

As shown, the equipment 10 can include an article of footwear 12. The footwear 12 can be of any suitable type for fitting to the foot 15 of the wearer 11. For instance, the footwear 12 can incorporate many of the features of a shoe, boot, sandal, or other types of footwear 12. As such, the footwear 12 can include an upper 14. The upper 14 can include one or more sheets or panels of material that are interconnected to define a cavity that receives the foot 15. Also, the upper 14 can include laces, buckles, pile tape, or other suitable types of means of securing the upper 14 to the foot 15.

In addition, the article of footwear 12 can include a sole assembly 16 that is operably coupled (e.g., lasted) to the upper 14. The sole assembly 16 can generally include an outsole for providing traction and a midsole for providing cushioned support for the wearer 11.

Moreover, the article of footwear 12 can include one or more traction elements 18, such as cleats or spikes. The traction elements 18 can be removably or integrally coupled to the sole assembly 16 and can penetrate the ground surface in order to further increase traction for the wearer 11.

Still further, the article of athletic equipment 10 can include a knee coupling member 20 that operably couples to a knee joint 21 of the leg 13. The knee coupling member 20 can include an anterior portion 22 that extends over and substantially covers the anterior portion of the knee joint 21. The anterior portion 21 can be a flexible sheet of material and, in some embodiments, the anterior portion 21 can be resiliently flexible. The anterior portion 22 can also include a hole 24 that can be centered on the knee cap of the knee joint 21.

Furthermore, the knee coupling member 20 can include a superior strap 26 that is fixed at each end to the anterior portion 21 and that extends (i.e., wraps) about the posterior portion of the knee joint 21, superior to a rotational axis of the knee joint 21. On the other hand, the knee coupling member 20 can also include an inferior strap 28 that is fixed at each end to the anterior portion 21 and that extends (i.e., wraps) about the posterior portion of the knee joint 21, inferior to the bending axis of the knee joint 21.

The straps 26, 28 can each be flexible, and in some cases resiliently flexible. Also, the straps 26, 28 can be integrally connected to the anterior portion 22 or, in other embodiments, the straps 26, 28 can be removably coupled to the anterior portion 22.

It will be appreciated that the knee coupling member 20 can be coupled about the knee joint 21 in a very secure manner. This is because the knee coupling member 20 extends superiorly and inferiorly about the knee joint 21. As such, the knee coupling member 20 can articulate within the knee coupling member 20, and the knee coupling member 20 is likely to remain secured to the knee joint 21. Furthermore, the hole 24 receives the knee cap of the knee joint 21 such that the knee coupling member 20 remains centered on the knee joint 21, even while the knee joint 21 articulates.

Furthermore, the equipment 10 can include a biasing member 30. The biasing member 30 can be elongate so as to extend between the article of footwear 12 and the knee coupling member 20. Moreover, in some embodiments, the biasing member 30 can include a first portion 32 and a second portion 34. At least one of the first and second portions 30, 32 can be resiliently flexible. For instance, in some embodiments, each of the first and second portions 30, 32 can be an elastic band. The first portion 32 can be coupled to the footwear 12 adjacent a heel portion 33 or other portion of the article of footwear. The second portion 34 can be coupled to the inferior strap 28 or other portion of the knee coupling member 20. The first and second portions 32, 34 can be coupled to the footwear 12 and the inferior strap 28, respectively, via stitching, adhesives, tape, or any other manner. Also, the biasing member 30 can include an adjustment member 36 that can operably couple the first and second portions 30, 32 and can be adjustable to vary a biasing load of the biasing member 30. In other embodiments, the biasing member 30 can extend continuously between the article of footwear 12 and the knee coupling member 20 and is not adjustable.

In some embodiments, the adjustment member 36 can be a buckle 38. As such, both the first and second portions 30, 32 can be operably coupled to (e.g., cinched to or looped around) the buckle 38 such that the first and second portions 30, 32 are in tension. To increase the amount of tension in the biasing member 30, the first and/or second portion 30, 32 can be cinched tighter around the buckle 38, and to reduce the amount of tension in the biasing member 30, the first and/or second portion 30, 32 can be released partially by the buckle 38. Accordingly, by changing the overall free length of the biasing member 30, the tension therein can be changed. It will be appreciated that the adjustment member 36 can be of any type other than the buckle 38. For instance, the adjustment member 36 can be pile tape (e.g., VELCRO™) for releasably and adjustably coupling the first and second portions 30, 32.

As shown in FIGS. 2 and 3, the biasing member 30 can extend along a longitudinal axis X of the leg 13 along a posterior side 39 of the leg 13, substantially parallel to the Achilles tendon (not specifically shown). Furthermore, as mentioned above, the biasing member 30 can be pre-tensioned so as to bias the footwear 12 and the knee coupling member 20 toward each other.

As shown in FIGS. 2 and 3, the equipment 10 can be worn while the wearer 11 moves, such as while running. As such, the article of footwear 12 can be positioned in a standing position (FIG. 2), in which the foot 15 and footwear 12 is substantially perpendicular to the axis X of the leg 13, and the article of footwear 12 can also be positioned in a plantarflexed position (FIG. 3), in which the foot 15 and the footwear 12 are plantarflexed (i.e., at an obtuse angle) relative to the leg 13. In some embodiments, the biasing member 30 remains in tension in both the standing position (FIG. 2) and in the plantarflexed position (FIG. 3) of the footwear 12. Furthermore, in some embodiments, the biasing member 30 remains in tension throughout the entire range of motion of the footwear 12.

Accordingly, when the footwear 12 is in the standing position (FIG. 2), the biasing member 30 can have an overall length L and can be in an elevated state of tension. Then, when the foot 15 is lifted (FIG. 3), the biasing member 30 can resiliently shorten to length L' and bias the heel portion 33 toward the knee coupling member 20, thereby facilitating earlier plantarflexion of the foot 15 and footwear 12 than would occur naturally without the equipment 10. Accordingly, while running, the foot 15 and the footwear 12 can be biased toward plantarflexion relative to the leg 13 every time the foot 15 and footwear 12 are lifted from the ground surface. As such, the wearer 11 is more likely to run on his or her toes.

By wearing the equipment 10 repeatedly over an extended period of time (e.g., several weeks or months), the wearer 11 can benefit due to resultant proprioceptive training. More specifically, by wearing the equipment 10 while running, the biased plantarflexion will eventually train the muscles to plantarflex the foot 15 more quickly during the running movement. Eventually, this increased plantarflexion can occur subconsciously, even without wearing the equipment 10. Thus, the running performance of the wearer can be improved.

It will also be appreciated that the equipment 10 can provide better fit and comfort for the wearer 11. For instance, even though the biasing member 30 biases the footwear 12 and the knee coupling member 20 toward each other, both the footwear 12 and the knee coupling member 20 are likely to remain in their respective intended positions. For instance, the footwear 12 is likely to remain secured to the foot 15 because the footwear 12 can be secured about substantially the entire foot 15. Likewise, the knee coupling member 20 is unlikely to slide down the leg 13 because the knee coupling member 20 is secured superiorly about the knee joint 21, and despite articulation of the knee joint 21, the knee coupling member 20 can remain secured superiorly about the knee joint 21.

Additionally, the biasing member 30 can be conveniently adjusted to vary the tension therein. As such, the proprioceptive training can be varied using the adjustment member 36 as discussed above.

Referring now to FIGS. 4 and 5, the article of athletic equipment 110 is illustrated according to various additional exemplary embodiments of the present disclosure. Components that are similar to the embodiments of FIG. 1-3 are indicated with corresponding reference numerals increased by 100.

As shown, the equipment 110 can include an article of footwear 112. The equipment 110 can also include a cuff 140 that extends continuously about and encircles the leg 113 (FIG. 4). The cuff 140 can be separated at a distance from the article of footwear 112 and can be sufficiently tightened about the leg 113 so as to be secured thereto. In some embodiments, the cuff 140 can be disposed inferior to the knee joint 121 (FIG. 4); however, in other embodiments, the cuff 140 can be disposed superior to the knee joint 121.

The equipment 110 can further include a biasing member 130 similar to the embodiments discussed above. In the embodiments shown, the biasing member 130 can be a continuous elastic band that extends between the footwear 112 and the cuff 140.

Moreover, the equipment 110 can include an anterior member 142 that is operably coupled to both the footwear 112 and the cuff 140. The anterior member 142 can extend along and substantially cover an anterior portion 143 of the leg 113 (FIG. 4). Also, the anterior member 142 can be substantially rigid. As such, the anterior member 142 can hold the cuff 140 separated from the footwear 112 and keep the biasing member 130 in tension. As an added bonus, the anterior member 142 can protect the anterior portion 143 of the leg 113, similar to a shin guard for a soccer or football player.

Thus, as shown in FIG. 5, the footwear 112 can be dorsiflexed to decrease the angle a relative to the leg 113. As such, the leg 113 can push against the anterior member 142, and tension in the biasing member 130 can increase. As described above, once the footwear 112 is lifted off the ground surface, the biasing member 130 can bias the footwear 112 toward plantarflexion. Thus, similar to the embodiments of FIGS. 1-3, the equipment 110 of FIGS. 4 and 5 can improve proprioception. Furthermore, the equipment 110 can securely fit to the leg 113 and foot 115 such that the equipment 110 can have sufficient comfort and can remain in position over the range of motion of the leg 113 and foot 115.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of proprioceptive training using an article of athletic equipment having an article of footwear, a knee coupling member, and a biasing member, the method comprising:
   securing the article of footwear to a foot;
   securing the knee coupling member to a leg superiorly and inferiorly about a knee joint of the leg; and
   biasing the article of footwear relative to the knee coupling member using the biasing member to bias the foot toward plantarflexion relative to the leg to increase proprioception of the foot relative to the leg.

2. The method of claim 1, wherein biasing includes lifting the foot from a ground surface to bias the foot toward plantarflexion.

3. The method of claim 2, further comprising running to bias the foot toward plantarflexion.

4. The method of claim 1, further comprising adjusting a tension of the biasing member to adjust the biasing of the article of footwear relative to the knee coupling member.

5. The method of claim 4, wherein adjusting the tension includes adjusting a first portion of the biasing member relative to a second portion of the biasing member to change a length of the biasing member.

6. The method of claim 4, wherein the biasing member is resilient and flexible, and wherein adjusting the tension includes changing a length of the biasing member.

7. The method of claim 1, further comprising extending the biasing member along a longitudinal axis of the leg along a posterior side of the leg.

8. The method of claim 1, further comprising extending the biasing member from a first area on the knee coupling member to a second area on the article of footwear.

9. The method of claim 8, wherein the second area is disposed on a heel portion of the article of footwear, and wherein extending the biasing member includes extending the biasing member from the first area to the heel portion of the article of footwear.

10. The method of claim 8, wherein the knee coupling member includes a superior strap that extends across a superior portion of the knee joint and an inferior strap that extends across an inferior portion of the knee joint, and
   wherein the first area is disposed on the inferior portion and is spaced apart at a distance from the superior strap, and
   wherein extending the biasing member includes extending the biasing member from the inferior strap to the second area on the article of footwear.

11. A method of proprioceptive training using an article of athletic equipment having an article of footwear, a knee coupling member, and a biasing member, the method comprising:

securing the article of footwear to a foot;

securing the knee coupling member to a leg superiorly and inferiorly about a knee joint thereof;

extending the biasing member between a heel portion of the article of footwear, along a longitudinal axis of the leg, along a posterior of the leg, to the knee coupling member; and biasing the article of footwear relative to the knee coupling member using the biasing member to bias the foot toward plantarflexion relative to the leg to increase proprioception of the foot relative to the leg.

12. The method of claim 11, wherein the knee coupling member includes an inferior strap and a superior strap, wherein securing the knee coupling member includes securing the inferior strap to the leg, inferior to the knee joint, wherein securing the knee coupling member includes securing the superior strap to the leg, superior to the knee joint, wherein extending the biasing member includes extending the biasing member from the heel portion of the article of footwear to the inferior strap of the knee coupling member.

13. The method of claim 11, further comprising adjusting a tension of the biasing member to adjust the biasing of the article of footwear relative to the knee coupling member.

14. The method of claim 13, wherein adjusting the tension includes adjusting a first portion of the biasing member relative to a second portion of the biasing member to change a length of the biasing member.

15. The method of claim 13, wherein the biasing member is resilient and flexible, and wherein adjusting the tension includes changing a length of the biasing member.

16. The method of claim 11, wherein biasing includes lifting the foot from a ground surface to bias the foot toward plantarflexion.

17. The method of claim 16, further comprising running to bias the foot toward plantarflexion.

18. A method of proprioceptive training using an article of athletic equipment having an article of footwear with a heel portion, a knee coupling member with an inferior strap and a superior strap, and a biasing member, the method comprising:

securing the article of footwear to a foot;

securing the inferior strap of the knee coupling member to a leg inferiorly relative to a knee joint of the leg;

securing the superior strap of the knee coupling member to the leg superiorly relative to the knee joint;

extending the biasing member between the heel portion of the article of footwear to the inferior strap of the knee coupling member, the biasing member extending along a longitudinal axis of the leg and along the posterior of the leg, the biasing member being separated at a distance from the superior strap; and biasing the article of footwear relative to the knee coupling member using the biasing member to bias the foot toward plantarflexion relative to the leg to increase proprioception of the foot relative to the leg.

19. The method of claim 18, further comprising adjusting a tension of the biasing member to adjust the biasing of the article of footwear relative to the knee coupling member.

20. The method of claim 19, wherein the biasing member is resilient and flexible, and wherein adjusting the tension includes adjusting a first portion of the biasing member relative to a second portion of the biasing member to change a length of the biasing member.

* * * * *